(12) United States Patent
Rouvinen et al.

(10) Patent No.: US 10,874,312 B2
(45) Date of Patent: Dec. 29, 2020

(54) USER WEARABLE APPARATUS WITH OPTICAL SENSOR

(71) Applicant: Nokia Technologies Oy, Espoo (FI)

(72) Inventors: Jarkko Rouvinen, Espoo (FI); Matti Kosonen, Jarvenpaa (FI)

(73) Assignee: Nokia Technolgies Oy, Espoo (FI)

( * ) Notice: Subject to any disclaimer, the term of this patent is extended or adjusted under 35 U.S.C. 154(b) by 603 days.

(21) Appl. No.: 15/553,015

(22) PCT Filed: Feb. 15, 2016

(86) PCT No.: PCT/FI2016/050091
§ 371 (c)(1),
(2) Date: Aug. 23, 2017

(87) PCT Pub. No.: WO2016/139390
PCT Pub. Date: Sep. 9, 2016

(65) Prior Publication Data
US 2018/0035905 A1    Feb. 8, 2018

(30) Foreign Application Priority Data

Mar. 3, 2015 (EP) .................................. 15157297

(51) Int. Cl.
*A61B 5/02* (2006.01)
*A61B 5/024* (2006.01)
(Continued)

(52) U.S. Cl.
CPC ...... *A61B 5/02438* (2013.01); *A61B 5/02427* (2013.01); *A61B 5/1455* (2013.01);
(Continued)

(58) Field of Classification Search
CPC . A61B 5/02438; A61B 5/1455; A61B 5/6829; A61B 5/02427; A61B 5/6804;
(Continued)

(56) References Cited

U.S. PATENT DOCUMENTS 5,238,000 A    8/1993   Niwa
9,311,792 B2   4/2016   Kosonen et al.
(Continued)

FOREIGN PATENT DOCUMENTS

EP    3026523 A1    6/2016
JP    H02095433 A   4/1990
(Continued)

OTHER PUBLICATIONS

"Do Wristband Heart Trackers Actually Work? A Checkup", Cnet, Retrieved on Aug. 16, 2017, Webpage available at : https://www.cnet.com/news/how-accurate-are-wristband-heart-rate-monitors/.
(Continued)

*Primary Examiner* — Christian Jang
(74) *Attorney, Agent, or Firm* — Harrington & Smith (57) ABSTRACT

A user wearable apparatus including an optical sensor structure configured to optically monitor an area of a body of a user wearing the apparatus to monitor a physiological property of the user. A movement of at least one part of the optical sensor structure is caused to change the monitored area of the body of the user and to determine a desired monitoring area, and thereafter the monitoring of the physiological property of the user is maintained at the determined desired monitoring area.

18 Claims, 6 Drawing Sheets

(51) Int. Cl.
*A61B 5/00* (2006.01)
*A61B 5/1455* (2006.01)

(52) U.S. Cl.
CPC ............ *A61B 5/681* (2013.01); *A61B 5/6804* (2013.01); *A61B 5/6829* (2013.01); *A61B 5/14552* (2013.01); *A61B 5/6823* (2013.01); *A61B 5/6824* (2013.01)

(58) Field of Classification Search
CPC ..... A61B 5/681; A61B 5/6823; A61B 5/6824; A61B 5/14552
See application file for complete search history.

(56) References Cited

U.S. PATENT DOCUMENTS

| | | | |
|---|---|---|---|
| 2011/0221657 | A1 | 9/2011 | Haddick et al. |
| 2014/0088433 | A1 | 3/2014 | Shan |
| 2014/0107493 | A1 | 4/2014 | Yuen et al. |
| 2014/0180039 | A1 | 6/2014 | Leboeuf et al. |
| 2014/0275852 | A1 | 9/2014 | Hong et al. |
| 2014/0275854 | A1* | 9/2014 | Venkatraman ......... A61B 5/721 600/301 |
| 2015/0038853 | A1 | 2/2015 | Pekonen |

FOREIGN PATENT DOCUMENTS

| | | |
|---|---|---|
| JP | H04051908 A | 2/1992 |
| JP | 2003325463 A | 11/2003 |
| JP | 2006271896 A | 10/2006 |
| JP | 2007330638 A | 12/2007 |
| JP | 2009072407 A | 4/2009 |
| JP | 2009254523 A | 11/2009 |
| WO | 2006/067690 A2 | 6/2006 |
| WO | 2016/083665 A1 | 6/2016 |

OTHER PUBLICATIONS

"Move With Meaning", MioGlobal, Retrieved on Aug. 21, 2017, Webpage available at : https://www.mioglobal.com/.
"Optical Heart Rate Sensor Design", Valencell, Retrieved on Aug. 21, 2017, Webpage available at : http://valencell.com/technology/.
"Heart Rate Monitor", Pulse on, Retrieved on Aug. 21, 2017, Webpage available at : http://pulseon.com/pulseon-color-cloud.html.
Wang et al., "Multichannel Reflective PPG Earpiece Sensor With Passive Motion Cancellation", IEEE Transactions on Biomedical Circuits and Systems, vol. 1, No. 4, Dec. 2007, pp. 235-241.
Extended European Search Report received for corresponding European Patent Application No. 15157297.1, dated Aug. 28, 2015, 4 pages.
International Search Report and Written Opinion received for corresponding Patent Cooperation Treaty Application No. PCT/FI2016/050091, dated May 4, 2016, 9 pages.
Office action received for corresponding European Patent Application No. 15157297.1, dated Sep. 18, 2018, 4 pages.
Office action received for corresponding Japanese Patent Application No. 2017-545576, dated Feb. 27, 2019, 6 pages of office action and 5 pages of translation available.
Office action received for corresponding Japanese Patent Application No. 2017-545576, dated Jul. 20, 2018, 6 pages of office action and 7 pages of translation available.

* cited by examiner

USER WEARABLE APPARATUS WITH OPTICAL SENSOR

RELATED APPLICATION

This application was originally filed as Patent Cooperation Treaty Application No. PCT/FI2016/050091 filed Feb. 15, 2016 which claims priority benefit to EP Patent Application No. 15157297.1, filed Mar. 3, 2015.

TECHNICAL FIELD

The present application generally relates to user wearable sensor apparatuses and especially to optical sensor arrangements therein.

BACKGROUND

This section illustrates useful background information without admission of any technique described herein representative of the state of the art.

Various metering devices such as pulse sensors have become more common for people to measure their own heart rate, movements or other parameters.

Pulse or heart rate measurement can be performed using a chest strap that is worn under clothes and maintains electric cardiac sensor's sensor in place on the skin of the user so that heart beat can be computed from the signals produced by the sensor. Another alternative is a wrist worn watch-like pulse sensor, often combined with accelerometers for acting as pedometer.

In wrist worn sensors, heart rate can be monitored for example optically. Optical heart rate measurement requires that the sensor is kept very stably on the wrist during the measurement. However, a wrist strap cannot be kept too tight, because it would be inconvenient/unpleasant for the user and might even stop or deteriorate blood circulation in small vessels thereby causing the measurement signal to disappear. As you need to be moderate with tightening, the device will basically always move a bit and the measurement is affected.

SUMMARY

Various aspects of examples of the invention are set out in the claims.

According to a first example aspect of the present invention, there is provided a user wearable apparatus comprising:
an optical sensor structure configured to optically monitor an area of a body of
a user wearing the apparatus to monitor a physiological property of the user, and
a processor configured
to cause movement of at least one part of the optical sensor structure to change the monitored area of the body of the user and to determine a desired monitoring area, and
to maintain the monitoring of the physiological property of the user at the determined desired monitoring area.

In an embodiment, the optical sensor structure comprises a light source configured to illuminate an area of the body of the user wearing the apparatus, and a detector configured to detect light rays reflected from the body of the user to monitor the physiological property of the user.

In an embodiment, the movement of the at least one part of the optical sensor structure causes changes in optical path of light rays used in the optical sensor structure.

In an embodiment, the movement of the at least one part of the optical sensor structure comprises movement of the whole optical sensor structure.

In an embodiment, the optical sensor structure comprises an actuator configured to move the at least one part of the optical sensor structure, and wherein the processor is configured to control the actuator to move the at least one part of the optical sensor structure.

In an embodiment, the at least one part of the optical sensor structure is moved laterally in relation to optical axis of the optical sensor structure.

In an embodiment, the movement of the at least one part of the optical sensor structure is movement of an internal structure of the at least one part of the optical sensor structure.

In an embodiment, the optical sensor structure comprises an optical emitter and emitter optics; and an optical detector and detector optics; and the actuator is configured to move at least one of: the optical emitter, the emitter optics, the optical detector, and the detector optics.

In an embodiment, the actuator is a stabilizer comprised in or operatively connected to a movable part of the optical sensor structure.

In an embodiment, the processor is configured to cause movement of the at least one part of the optical sensor structure to compensate for movements of the user wearable apparatus and to maintain the monitoring of the physiological property of the user at the determined desired monitoring area.

In an embodiment, the user wearable apparatus further comprises a motion detection sensor configured to detect movements of the user wearable apparatus in relation to the body of the user, and the processor is configured to determine, based on movements detected by the motion detection sensor, movement required for the at least one part of the optical sensor structure to compensate for the movements of the user wearable apparatus.

In an embodiment, the desired monitoring area is an area that fulfills certain predefined criteria.

In an embodiment, the physiological property is heart rate.

In an embodiment, the apparatus is one of: a wrist strap, an ankle strap, a device configured to be integrated into a garment of a user.

According to a second example aspect of the present invention, there is provided a method comprising:
using an optical sensor structure to optically monitor an area of a body of a user wearing a user wearable apparatus to monitor a physiological property of the user,
moving at least one part of the optical sensor structure to change the monitored area of the body of the user and to determine a desired monitoring area, and
maintaining the monitoring of the physiological property of the user at the determined desired monitoring area.

In an embodiment, the method comprises moving the at least one part of the optical sensor structure to compensate for movements of the user wearable apparatus and to maintain the monitoring of the physiological property of the user at the determined desired monitoring area.

In an embodiment, the method further comprises detecting movements of the user wearable apparatus in relation to the body of the user, and determining, based on movements detected, movements required for the at least one part of the optical sensor structure to compensate for the movements of the user wearable apparatus.

According to a third example aspect of the present invention, there is provided a computer program comprising computer executable program code configured to control a wearable device, when the computer executable program code is executed, to perform the method of the second aspect.

The computer program may be stored in a computer readable memory medium. The memory medium may be a non-transitory memory medium.

Any foregoing memory medium may comprise a digital data storage such as a data disc or diskette, optical storage, magnetic storage, holographic storage, optomagnetic storage, phase-change memory, resistive random access memory, magnetic random access memory, solid-electrolyte memory, ferroelectric random access memory, organic memory or polymer memory. The memory medium may be formed into a device without other substantial functions than storing memory or it may be formed as part of a device with other functions, including but not limited to a memory of a computer, a chip set, and a sub assembly of an electronic device.

Different non-binding example aspects and embodiments of the present invention have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE DRAWINGS

Example embodiments of the present invention and its potential advantages are understood by referring to FIGS. 1 through 6 of the drawings. In this document, like reference signs denote like parts or steps.

In the following, various example embodiments are discussed in connection with heart rate monitoring. Various embodiments are however not necessarily limited to heart rate monitoring only. Instead some other physiological condition can be monitored instead or in addition to heart rate monitoring. Physiological conditions may include one or more of the following: heart rate, blood pressure, and CO2 (carbon dioxide) level. Also other physiological condition measurements may apply.

Figure 1:
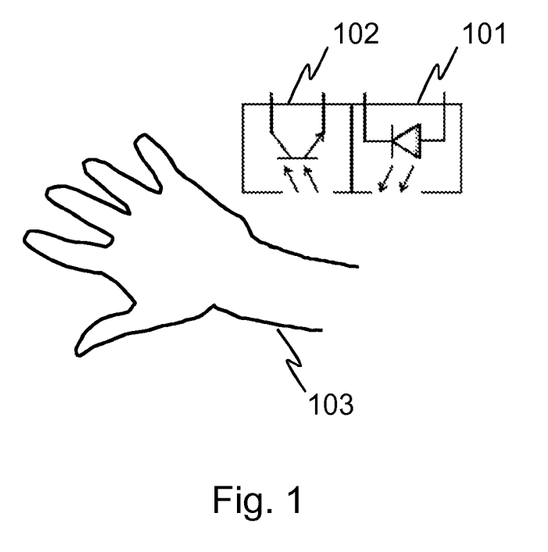
FIG. 1 is a simplified illustration of an example optical heart rate measurement.

Heart rate can be monitored optically by measuring variations in blood volume with a PPG (Photoplethymography) sensor. FIG. 1 is a simplified illustration of an example optical heart rate measurement. FIG. 1 shows a simple reflective type PPG sensor that comprises a LED (light emitting diode) 101 and a photo diode (light detector) 102. The LED (optical emitter, light source) 101 emits light and the detector 102 receives light rays reflected from a wrist 103 of a user. Such optical heart rate measurement requires that the sensor is kept very stably on the wrist during the measurement. However, a wrist strap cannot be kept too tight, because it would be inconvenient/unpleasant for the user and might even stop or deteriorate blood circulation in small vessels thereby causing the measurement signal to disappear. As you need to be moderate with tightening, the device will basically always move a bit and the measurement is affected.

In an embodiment of the invention, a monitoring apparatus (such as a heart rate monitoring device) is arranged to alter or change optical path of light rays used in an optical sensor structure before the light rays hit a detector element of the optical sensor structure. In an embodiment, the changes in the optical path are caused by moving part of the optical sensor structure (without moving the whole apparatus). In general, the optical sensor structure of such monitoring apparatus comprises a light source configured to illuminate an area of the body of the user wearing the apparatus, and a detector configured to detect light rays reflected from the body of the user to monitor the physiological property of the user.

The monitoring apparatus monitors a certain area of a body of a user. In an embodiment, at least one (internal) part of the optical sensor structure is moved to different positions to find a desired monitoring area. The movements are internal movements that do not move the whole monitoring apparatus. In an embodiment, the optical path of light rays used in the optical sensor structure is changed to find a desired monitoring area. The desired monitoring area may for example fulfill certain predefined criteria and/or be an optimal monitoring area. In an example, an area where the measured signal is strongest or where the signal exceeds certain threshold value is searched for. The threshold may be for example such that exceeding the threshold fulfills quality requirements set for the measurement. When the desired monitoring area has been found, the measurements are locked to that area. Thereafter changes in optical path of light rays used in the optical sensor structure and/or internal movements of internal part(s) of the optical sensor structure may be used to compensate for movements of the monitoring apparatus in relation to the body of the user. In this way the measurements can be maintained at the desired monitoring area. This may improve the monitoring result.

The part of the optical sensor structure that is moved may be the detector, the optical elements of the sensor structure, or the light source elements of the sensor structure, or some other part whose movement alters the optical path of light rays used in the optical sensor structure. In an embodiment the whole optical sensor structure is moved to change the monitoring area.

There may be for example an actuator that causes the movements of the movable part of the optical sensor structure. The actuator may be a stabilizer comprised in or integrated into the part that is moved. The actuator may be an electromagnetic voice coil or a piezoelectric actuator, for example.

Figure 2A:
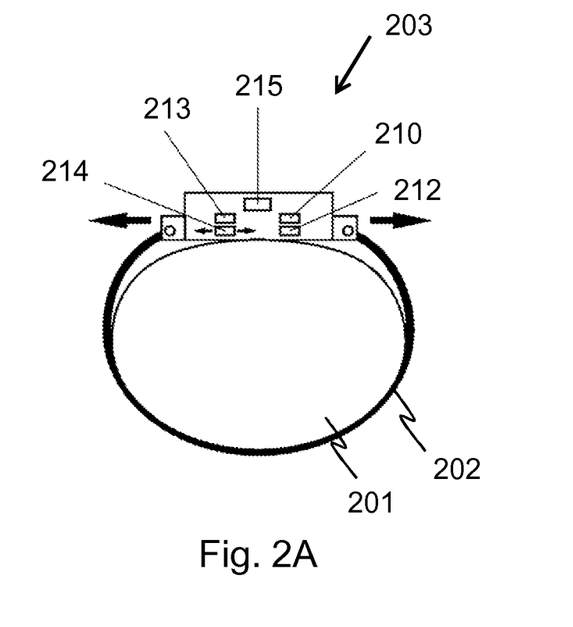
FIGS. 2A and 2B show schematic drawings of apparatuses of example embodiments.
Figure 2B:
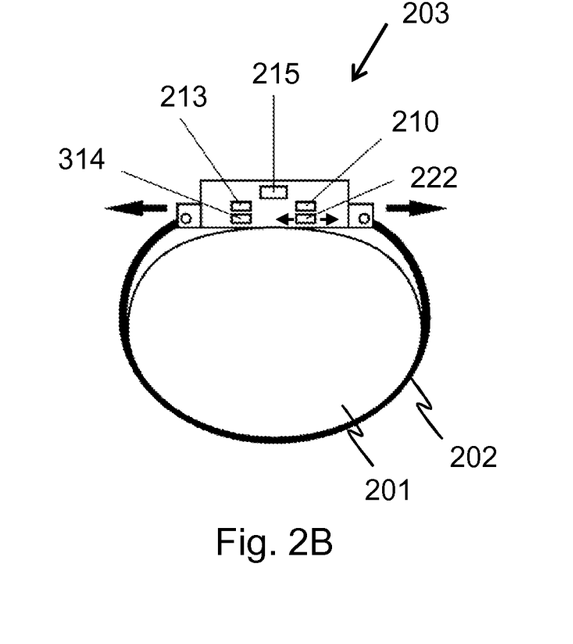

FIGS. 2A and 2B show schematic drawings of apparatuses of example embodiments. The apparatus is a user wearable device that comprises a strap 202 that can be fitted around a wrist 201 of a user and a body 203.

In FIG. 2A, the body 203 comprises an optical sensor structure comprising an optical emitter 210, emitter optics 212, detector 213 and detector optics 214. The optical sensor structure is configured to produce sensor signals corresponding to a property of the skin or underlying matter (capillaries and veins, for example). In the example of FIG. 2A the detector optics 214 comprises or is operatively connected to an actuator that is configured to move the detector optics 214 within the body 203 and the optical sensor structure. In an example one may define that the actuator causes the detector optics to move perpendicularly in relation to an optical axis of the detector optics to cause a change in optical path of light rays in the optical sensor structure. If the optical axis of the detector optics is denoted as z direction in three dimensional coordinates, the detector optics may move in x and y directions. In an example one may define that the actuator causes the detector optics to move laterally in relation to skin of the user wearing the apparatus to cause a change in optical path of light rays in the optical sensor structure. In an example embodiment the movement of the detector optics 214 is a movement within the detector optics, i.e. an internal movement of the movable component. For example if the detector optics comprises a shape-changing prism, the movement may be tilting of glass plates of the shape-changing prism.

Furthermore the body 203 comprises a motion detector 215. In addition, the body comprises a processor or some other processing unit (not shown) that is configured to control functionalities of the body and the optical sensor structure. The processor may process measurement values or sensor signals received from the motion detector and the optical sensor structure, and control the optical sensor structure accordingly. The processor may for example determine desired monitoring area for the optical sensor structure and/or maintain monitoring at the desired monitoring area. The processor may cause the actuator to move the detector optics to change monitoring area of the optical sensor structure in order to determine the desired monitoring area. Additionally, the processor may cause the actuator to move the detector optics to compensate for movements of the apparatus in order to maintain the monitoring at the desired monitoring area.

In an example embodiment the detector optics operates as an optical stabilizer in front of the detector 213. The detector optics/optical stabilizer may be any suitable lens element or a shape-changing prism, for example.

In FIG. 2B, the body 203 comprises an optical sensor structure comprising an optical emitter 210, emitter optics 222, detector 213 and detector optics 314. The optical sensor structure is configured to produce sensor signals corresponding to a property of the skin or underlying matter (capillaries and veins, for example). In the example of FIG. 2B the emitter optics 222 comprises or is operatively connected to an actuator that is configured to move the emitter optics 222 within the body 203 and the optical sensor structure. In an example one may define that the actuator causes the emitter optics to move perpendicularly in relation to an optical axis of the emitter optics to cause a change in optical path of light rays in the optical sensor structure. If the optical axis of the emitter optics is denoted as z direction in three dimensional coordinates, the emitter optics may move in x and y directions. In an example one may define that the actuator causes the emitter optics to move laterally in relation to skin of the user wearing the apparatus to cause a change in optical path of light rays in the optical sensor structure. In an example embodiment the movement of the emitter optics 222 is a movement within the emitter optics. For example if the emitter optics comprises a shape-changing prism, the movement may be tilting of glass plates of the shape-changing prism.

Furthermore the body 203 comprises a motion detector 215. In addition, the body comprises a processor or some other processing unit (not shown) that is configured to control functionalities of the body and the optical sensor structure. The processor may process measurement values or sensor signals received from the motion detector and the optical sensor structure, and control the optical sensor structure accordingly. The processor may for example determine desired monitoring area for the optical sensor structure and/or maintain monitoring at the desired monitoring area. The processor may cause the actuator to move the emitter optics to change monitoring area of the optical sensor structure in order to determine the desired monitoring area. Additionally, the processor may cause the actuator to move the emitter optics to compensate for movements of the apparatus in order to maintain the monitoring at the desired monitoring area.

In an example embodiment the emitter optics operates as an optical stabilizer in front of the emitter 210. The emitter optics/optical stabilizer may be any suitable lens element or a shape-changing prism, for example.

Figure 3A:
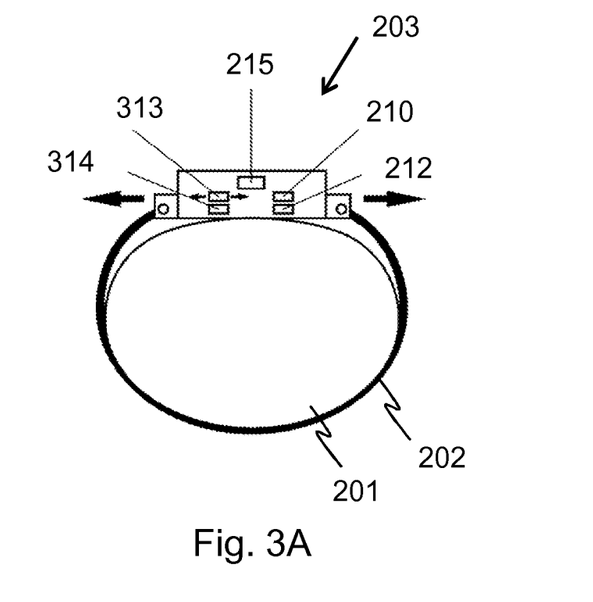
FIGS. 3A, 3B and 3C show schematic drawings of apparatuses of example embodiments.
Figure 3B:
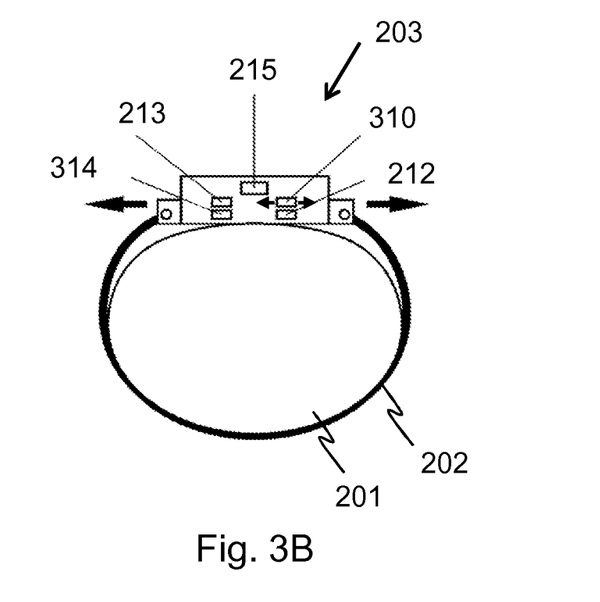
Figure 3C:
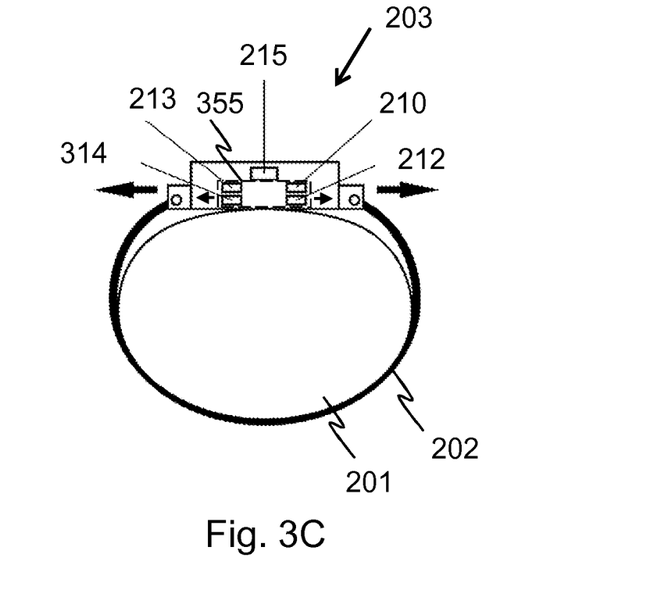

FIGS. 3A, 3B and 3C show schematic drawings of apparatuses of example embodiments. The apparatus is a user wearable device that comprises a strap 202 that can be fitted around a wrist 201 of a user and a body 203.

In FIG. 3A, the body 203 comprises an optical sensor structure comprising an optical emitter 210, emitter optics 212, detector 313 and detector optics 314. The optical sensor structure is configured to produce sensor signals corresponding to a property of the skin or underlying matter (capillaries and veins, for example). In the example of FIG. 3 the detector 313 comprises or is operatively connected to an actuator that is configured to move the detector 313 within the body 203 and the optical sensor structure. In an example one may define that the actuator causes the detector to move perpendicularly in relation to an optical axis of the optical sensor structure. If the optical axis of the optical sensor structure is denoted as z direction in three dimensional coordinates, the detector 313 may move in x and y directions. In an example one may define that the actuator causes the detector 313 to move laterally in relation to skin of the user wearing the apparatus. Moving the detector 313 changes the place/spot of the user's skin from where reflected light rays are detected by the sensor structure.

Furthermore the body 203 comprises a motion detector 215. In addition, the body comprises a processor or some other processing unit (not shown) that is configured to control functionalities of the body and the optical sensor structure. The processor may process measurement values or sensor signals received from the motion detector and the optical sensor structure, and control the optical sensor structure accordingly. The processor may for example determine desired monitoring area for the optical sensor structure and/or maintain monitoring at the desired monitoring area. The processor may cause the actuator to move the detector to change monitoring area of the optical sensor structure in order to determine the desired monitoring area. Additionally, the processor may cause the actuator to move the detector to compensate for movements of the apparatus in order to maintain the monitoring at the desired monitoring area.

In FIG. 3B, the body 203 comprises an optical sensor structure comprising an optical emitter 310, emitter optics 212, detector 213 and detector optics 314. The optical sensor structure is configured to produce sensor signals corresponding to a property of the skin or underlying matter (capillaries and veins, for example). In the example of FIG. 3B the optical emitter 310 comprises or is operatively connected to an actuator that is configured to move the optical emitter 310 within the body 203 and the optical sensor structure. In an example one may define that the actuator causes the optical emitter to move perpendicularly in relation to an optical axis of the optical sensor structure. If the optical axis of the optical sensor structure is denoted as z direction in three dimensional coordinates, the optical emitter 310 may move in x and y directions. In an example one may define that the actuator causes the optical emitter 310 to move laterally in relation to skin of the user wearing the apparatus. Moving the optical emitter 310 changes the place/spot of the user's skin from where reflected light rays are detected by the sensor structure.

Furthermore the body 203 comprises a motion detector 215. In addition, the body comprises a processor or some other processing unit (not shown) that is configured to control functionalities of the body and the optical sensor structure. The processor may process measurement values or sensor signals received from the motion detector and the optical sensor structure, and control the optical sensor structure accordingly. The processor may for example determine desired monitoring area for the optical sensor structure and/or maintain monitoring at the desired monitoring area. The processor may cause the actuator to move the optical emitter 310 to change monitoring area of the optical sensor structure in order to determine the desired monitoring area. Additionally, the processor may cause the actuator to move the optical emitter 310 to compensate for movements of the apparatus in order to maintain the monitoring at the desired monitoring area.

In FIG. 3C, the body 203 comprises an optical sensor structure 355 comprising an optical emitter 210, emitter optics 212, detector 213 and detector optics 314. The optical sensor structure is configured to produce sensor signals corresponding to a property of the skin or underlying matter (capillaries and veins, for example). In the example of FIG. 3C the optical sensor structure 355 comprises or is operatively connected to an actuator that is configured to move the optical sensor structure 355 within the body 203. In an example one may define that the actuator causes the optical sensor structure 355 to move perpendicularly in relation to an optical axis of the optical sensor structure. If the optical axis of the optical sensor structure is denoted as z direction in three dimensional coordinates, the optical sensor structure 355 may move in x and y directions. In an example one may define that the actuator causes the optical sensor structure 355 to move laterally in relation to skin of the user wearing the apparatus.

Furthermore the body 203 comprises a motion detector 215. In addition, the body comprises a processor or some other processing unit (not shown) that is configured to control functionalities of the body and the optical sensor structure. The processor may process measurement values or sensor signals received from the motion detector and the optical sensor structure, and control the optical sensor structure accordingly. The processor may for example determine desired monitoring area for the optical sensor structure and/or maintain monitoring at the desired monitoring area. The processor may cause the actuator to move the optical sensor structure 355 to change monitoring area of the optical sensor structure in order to determine the desired monitoring area. Additionally, the processor may cause the actuator to move the optical sensor structure 355 to compensate for movements of the apparatus in order to maintain the monitoring at the desired monitoring area.

FIGS. 2A-3B show examples where the movable part of the optical sensor structure is the detector or the detector optics or alternatively the optical emitter or emitter optics. Also some other part may be moved to cause changes in monitoring area of the optical sensor structure and/or to change the optical path of the optical sensor structure. The movement of the movable part may be a lateral movement or an internal movement inside the movable part.

It is noted that the apparatus of FIGS. 2A-3C may be shaped like a watch and it may be configured to display time or other useful information to the user. The body 203 of the apparatus may be made of any of metals; plastics; carbon fiber materials; glass; wood; ceramics; and any combination or composition thereof. The body 203 of the apparatus can be formed roughly as a concave block or unit or as a block or unit with a cut-out on one side thereof. The strap 202 may be made of suitable flexible or bendable material, such as plastic, fabric, and leather. In an example embodiment, the strap 202 and the body 203 are integrally formed of one piece of material. The material can comprise or consist of any of the following: plastics, metals, nano-fibers, carbon fiber, leather, and glass.

FIGS. 2A-3C show a wrist strap as an example apparatus. Alternatively an apparatus according to example embodiments of the invention may be some other device that is wearable by a user. The apparatus may be a device that is configured to be integrated into a garment of a user. The device may be attached or integrated for example to a belt, a sock, a shoe, a sleeve or a collar of a shirt or pullover, and/or a waistband of trousers or skirt. The device may be detachable from the garment.

Figure 4:
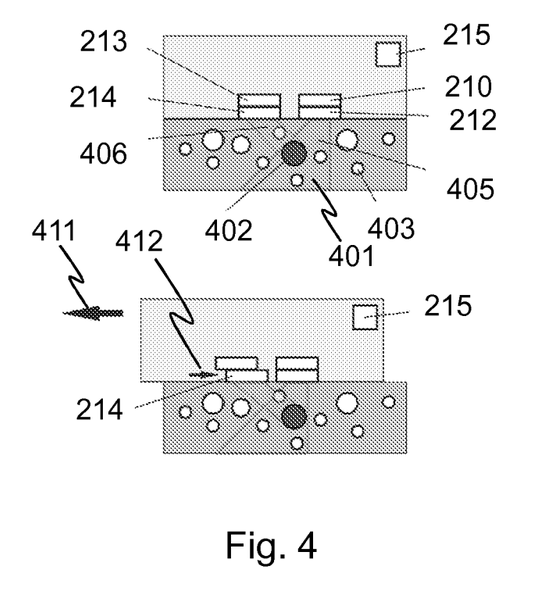
FIG. 4 illustrates operation principle of an example embodiment.

FIG. 4 illustrates operation principle of an example embodiment. The shown example is based on the apparatus of FIG. 2 where the detector optics 214 is movable.

In heart rate monitoring the optical sensor structure works as follows: the optical emitter 210 (e.g. a LED) illuminates certain area 401 of a wrist of a user. The apparatus (e.g. a processor therein) studies the volume of changes of blood vessels 402, 403. The detector 213 receives light rays 406 reflected from the wrist. If the apparatus moves in relation to the wrist, the reflected light rays come to the detector 213 from different area than earlier. This causes discontinuity and stops the measurement for a certain period. If the movement happens constantly, the apparatus is unable to perform the monitoring at all. This problem is removed by moving the detector optics and by thereby changing the optical path of the light rays. In the shown example, the apparatus moves in the direction of arrow 411. The movement is detected by the motion detector 215 and in order to compensate for the movement the detector optics 214 are caused to move in the direction of arrow 412 so that light rays from the same area, that was previously monitored, are folded to the detector. In this way light rays from the desired area (e.g. the most optimum area) are guided to the detector 213 regardless of the apparatus movement.

Figure 5:
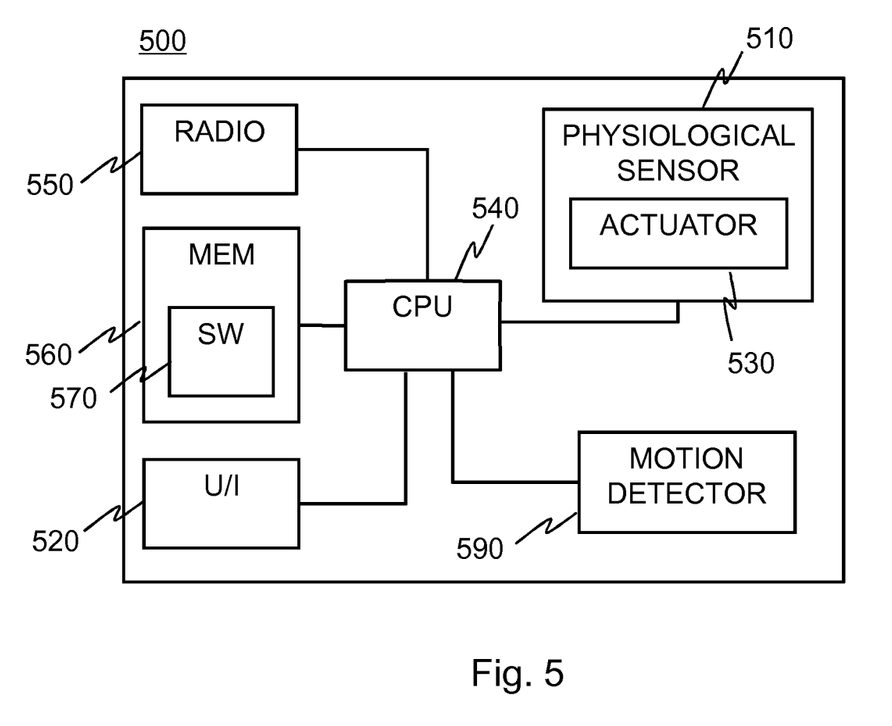
FIG. 5 shows a block diagram of an apparatus of an example embodiment.

FIG. 5 shows a block diagram of the apparatus 500 of an example embodiment, for helping understanding of various processing and control related aspects. The apparatus 500 can be suited for use as the apparatus of FIGS. 2 and 3.

The apparatus 500 comprises a radio unit 550, a processor 540 coupled to the radio unit 550, and a memory 560 coupled to the processor 540. The apparatus further comprises a motion detector 590, a physiological sensor 510, and a user interface (U/I) unit 520, such as a touch sensitive display, which are coupled to the processor 540.

The memory 560 comprises a work memory and a non-volatile memory such as a read-only memory, flash memory, optical or magnetic memory. In the memory 560, typically at least initially in the non-volatile memory, there is stored software 570 operable to be loaded into and executed by the processor 540. The software 570 may comprise one or more software modules and can be in the form of a computer program product that is software stored in a memory medium.

The radio unit 550 is configured to provide communications to other devices or communication networks over one or more links. The links may be wired and/or wireless links. The communication interface 550 may further or alternatively implement telecommunication links suited for establishing links with other users or for data transfer, e.g. using the Internet. Such telecommunication links may be links using any of: wireless local area network links, Bluetooth, ultra-wideband, cellular or satellite communication links.

The motion detector 590 is configured to detect movements of the apparatus 500 in relation to the body of the user. The motion detector may be for example an optical sensor or an accelerometer.

The physiological sensor 510 is an optical sensor that is configured to monitor certain physiological property of a user wearing the apparatus 500. The physiological sensor 510 comprises an actuator 530 that is operable to move one or more internal parts or components of the physiological sensor 510. The movement caused by the actuator 510 may alter optical path of light rays used in the physiological sensor 510. The actuator 530 may move the part of the physiological sensor 510 without moving the whole sensor element 510. Alternatively, the actuator may move the whole sensor element 510 without moving the apparatus 500. The internal parts of the physiological sensor are not shown in FIG. 5 for the sake of clarity.

The processor 540 is, for instance, a central processing unit (CPU), a microprocessor, a digital signal processor (DSP), a graphics processing unit, an application specific integrated circuit (ASIC), a field programmable gate array, a microcontroller or a combination of such elements. In an example embodiment the processor is configured, in response to signals received from the motion detector 590 and/or the physiological sensor 510 to control the actuator 530 of the physiological sensor to move one or more internal parts of the physiological sensor 510 for example to alter optical path of light rays used in the physiological sensor 510. In an example embodiment the processor is configured to control the actuator 530 of the physiological sensor to move one or more internal parts of the physiological sensor 510 to change the monitored area of a body of a user of the apparatus 500 in order to determine a desired monitoring area. In an example embodiment the processor is configured to determine, based on movements detected by the motion detection sensor, movements required for internal parts of the physiological sensor 510 and/or changes required in the optical path of light rays used in the physiological sensor 510 to compensate for the movements of the apparatus 500.

A skilled person appreciates that in addition to the elements shown in FIG. 5, the apparatus 500 may comprise other elements, such as microphones, displays, and batteries.

It shall be understood that any coupling in this document refers to functional or operational coupling; there may be intervening components or circuitries in between coupled elements unless expressly otherwise described.

Figure 6:
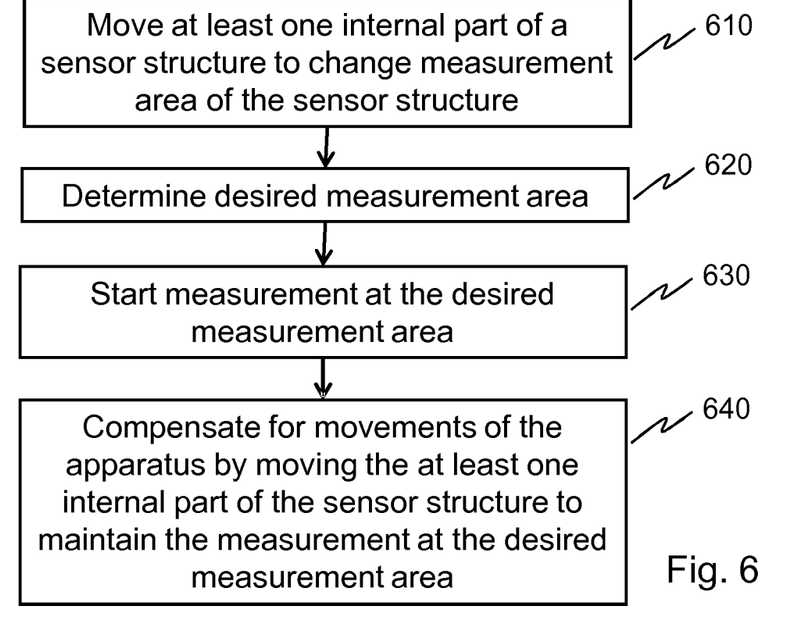
FIG. 6 shows a flow chart of a process of an example embodiment.

FIG. 6 shows a flow chart of a process of an example embodiment. The process comprises: 610 moving an internal part of a sensor structure to change measurement area of the sensor structure (e.g. an optical component, detector component, light source component or a suitable combination thereof may be moved); 620 determining desired measurement area (e.g. an area that fulfills certain predefined criteria, an area where one detects most optimal blood vessels for heart rate monitoring, or an area that exhibits strongest signal); 630 starting measurement at the desired measurement area (comprising for example locking the measurement to the desired area); and 640 compensating for movements of the apparatus by moving the at least one internal part of the sensor structure to maintain the measurement at the desired measurement area. In an example embodiment the whole sensor structure may be moved inside the apparatus to change the measurement area of the sensor structure or to compensate for the movements of the apparatus.

Figure 7:
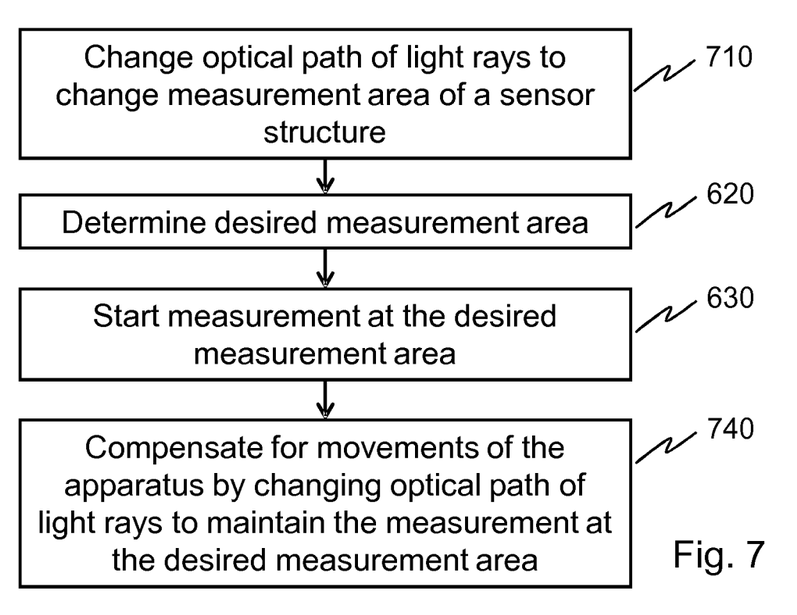
FIG. 7 shows a flow chart of a process of another example embodiment.

FIG. 7 shows a flow chart of a process of an example embodiment. The process comprises: 710 changing optical path of light rays to change measurement area of a sensor structure; 620 determining desired measurement area (e.g. an area that fulfills certain predefined criteria, an area where one detects most optimal blood vessels for heart rate monitoring, or an area that exhibits strongest signal); 630 starting measurement at the desired measurement area (comprising for example locking the measurement to the desired area); and 740 compensating for movements of the apparatus by changing optical path of light rays to maintain the measurement at the desired measurement area.

Without in any way limiting the scope, interpretation, or application of the claims appearing below, a technical effect of one or more of the example embodiments disclosed herein is that optical monitoring of physiological properties, such as heart rate, is improved. For example reliability of the monitoring is enhanced. Another technical effect of one or more of the example embodiments disclosed herein is that signal quality is improved as a monitoring area fulfilling predefined criteria or a monitoring area providing the best results is searched for before starting the monitoring. Another technical effect of one or more of the example embodiments disclosed herein is that the apparatus may be allowed to move without disturbing or stopping the monitoring process. Another technical effect of one or more of the example embodiments disclosed herein is that there is no need for electrical stabilization or compensation or other processing of results performed on the detected signals as the movements of the apparatus are compensated for before the light rays hit the detector.

If desired, the different functions discussed herein may be performed in a different order and/or concurrently with each other. Furthermore, if desired, one or more of the before-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the foregoing describes example embodiments of the invention, these descriptions should not be viewed in a limiting sense. Rather, there are several variations and modifications which may be made without departing from the scope of the present invention as defined in the appended claims.

The invention claimed is:

1. A user wearable apparatus; comprising:
   at least one processor; and
   at least one memory including computer program code, where the at least one memory and the computer program code are configured, with the at least one processor, to cause the apparatus to at least:
   use an optical sensor structure configured to optically monitor an area of a body of a user wearing the apparatus to monitor a physiological property of the user;
   detect a movement of at least one part of the optical sensor structure of the user wearable apparatus causing changes in optical path of light rays used in the optical sensor structure for the monitored area of the body of the user;
   based on the detected movement of the at least one part of the optical sensor structure causing changes in the optical path, determine a desired monitoring area of the body of the user, comprising:
   determining in response to the changes, an amount of movement of the at least part of the optical sensor structure required to compensate for the detected movement of the at least one part of the optical sensor structure of the user wearable apparatus and to improve the monitoring of the physiological property of the user at the determined desired monitoring area, wherein the movement is determined for at least one direction based on three dimensional coordinates; and
   maintaining the monitoring of the physiological property of the user at the determined desired monitoring area.

2. The user wearable apparatus according to claim 1, wherein the optical sensor structure comprises a light source configured to illuminate an area of the body of the user wearing the apparatus, and a detector configured to detect light rays reflected from the body of the user to monitor the physiological property of the user.

3. The user wearable apparatus according to claim 1, wherein the movement of the at least one part of the optical sensor structure comprises movement of the whole optical sensor structure.

4. The user wearable apparatus according to claim 1, wherein the optical sensor structure comprises an actuator configured to move the at least one part of the optical sensor structure, and wherein the at least one memory including the computer program code is configured with the at least one processor to cause the apparatus to control the actuator to move the at least one part of the optical sensor structure.

5. The user wearable apparatus according to claim 1, wherein the at least one part of the optical sensor structure is moved laterally in relation to optical axis of the optical sensor structure.

6. The user wearable apparatus according to claim 1, wherein the movement of the at least one part of the optical sensor structure is movement of an internal structure of the at least one part of the optical sensor structure.

7. The user wearable apparatus according to claim 1, wherein the optical sensor structure comprises an optical emitter and emitter optics; and an optical detector and detector optics; and wherein the actuator is configured to move at least one of: the optical emitter, the emitter optics, the optical detector, and the detector optics.

8. The user wearable apparatus according to claim 1, wherein the actuator is a stabilizer comprised in or operatively connected to a movable part of the optical sensor structure.

9. The user wearable apparatus according to claim 1, wherein the at least one memory including the computer program code is configured with the at least one processor to cause the apparatus to use a motion detection sensor configured to detect movements of the user wearable apparatus in relation to the body of the user, wherein the at least one memory including the computer program code is configured with the at least one processor to cause the apparatus to determine, based on movements detected by the motion detection sensor, movement required for the at least one part of the optical sensor structure to compensate for the movements of the user wearable apparatus.

10. The user wearable apparatus according to claim 1, wherein the desired monitoring area is an area that fulfills certain predefined criteria.

11. The user wearable apparatus according to claim 1, wherein the physiological property is heart rate.

12. The user wearable apparatus according to claim 1, wherein the apparatus is embodied in one of: a wrist strap, an ankle strap, a device configured to be integrated into a garment of a user.

13. A method comprising:
    using an optical sensor structure to optically monitor an area of a body of a user wearing a user wearable apparatus to monitor a physiological property of the user;
    detect movement of at least one part of the optical sensor structure of the user wearable apparatus causing changes in optical path of light rays used in the optical sensor structure for the monitored area of the body of the user;
    based on the detected movement of the at least one part of the optical sensor structure causing changes in the optical path, determine a desired monitoring area of the body of the user comprising:
    determining in response to the changes, an amount of movement of the at least part of the optical sensor structure required to compensate for the detected movement of the at least one part of the optical sensor structure of the user wearable apparatus and to improve the monitoring of the physiological property of the user at the determined desired monitoring area, wherein the movement is determined for at least one direction based on three dimensional coordinates; and
    maintaining the monitoring of the physiological property of the user at the determined desired monitoring area.

14. The method according to claim 13, wherein using the optical sensor structure comprises a light source illuminating an area of the body of the user wearing the apparatus, and a detector detecting light rays reflected from the body of the user to monitor the physiological property of the user.

15. The user wearable apparatus according to claim 13, wherein the movement of the at least one part of the optical sensor structure causes changes in optical path of light rays used in the optical sensor structure.

16. The user wearable apparatus according to claim 13, wherein the movement of the at least one part of the optical sensor structure comprises moving of the whole optical sensor structure.

17. The user wearable apparatus according to claim 13, wherein the optical sensor structure comprises an actuator moving the at least one part of the optical sensor structure, and wherein the processor is controlling the actuator to move the at least one part of the optical sensor structure.

18. The user wearable apparatus according to claim 13, wherein the at least one part of the optical sensor structure is moving laterally in relation to optical axis of the optical sensor structure.

\* \* \* \* \*